(12) United States Patent
Todd et al.

(10) Patent No.: US 8,617,850 B2
(45) Date of Patent: Dec. 31, 2013

(54) OLIGONUCLEOTIDES FOR DETECTING CHICKEN ASTROVIRUS

(75) Inventors: Daniel Todd, Belfast (GB); Victoria Jane Smyth, Belfast (GB)

(73) Assignee: Agri-Food Biosciences Institute, Belfast (GB)

( * ) Notice: Subject to any disclaimer, the term of this patent is extended or adjusted under 35 U.S.C. 154(b) by 0 days.

(21) Appl. No.: 13/384,712

(22) PCT Filed: Jul. 23, 2010

(86) PCT No.: PCT/GB2010/051226
§ 371 (c)(1),
(2), (4) Date: Feb. 16, 2012

(87) PCT Pub. No.: WO2011/010168
PCT Pub. Date: Jan. 27, 2011

(65) Prior Publication Data
US 2012/0141979 A1   Jun. 7, 2012

(30) Foreign Application Priority Data

Jul. 24, 2009 (GB) .................................. 0912950.3

(51) Int. Cl.
*C12P 19/34* (2006.01)
*C07H 21/04* (2006.01)

(52) U.S. Cl.
USPC ........................ 435/91.2; 536/24.3; 536/24.33

(58) Field of Classification Search
USPC .............................. 435/91.2; 536/24.3, 24.33
See application file for complete search history.

(56) References Cited

U.S. PATENT DOCUMENTS 5,994,056 A   11/1999   Higuchi
6,171,785 B1   1/2001   Higuchi

FOREIGN PATENT DOCUMENTS

WO   WO-2006/085407 A1   8/2006
WO   WO-2007/077464 A2   7/2007

OTHER PUBLICATIONS

Persson, Anna, "International Search Report" for PCT/GB2010/051226, as mailed Oct. 26, 2010, 5 pages.
Esumi, M. et al, "Method of screening a gene related to a quantity of HCV", Mar. 5, 2007, 1 page.
Todd, D et al, "Identification of chicken enterovirus-like viruses, duck hepatitis virus type 2 and duck hepatitis virus type 3 as astroviruses", Avian Pathology, Feb. 2009, 38(1), pp. 21-29.
Pantin-Jackwood, Mary J. et al, "Molecular Characterization and Typing of Chicken and Turkey Astroviruses Circulating in the United States: Implications for Diagnostics", Avian Diseases, 2006, 50: 397-404.
Baxendale, W. et al, "The isolation and characterisation of astroviruses from chickens", Avian Pathology, Jun. 2004, 33(3), 364-370.
Smyth, V.J. et al, "Detection of chicken astrovirus by reverse transcriptase-polymerase chain reaction", Avian Pathology, Aug. 2009 38(4), pp. 293-299.
Day,J.M. et al, "A Multiplex RT-PCR Test for the Differential Identification of Turkey Astrovirus Type 1, Turkey Astrovirus Type 2, Chicken Astrovirus, Avian Nephritis Virus, and Avian Rotavirus", Avian Diseases, 2007, 51:681-684.

*Primary Examiner* — Cynthia B Wilder
(74) *Attorney, Agent, or Firm* — Winstead PC

(57) ABSTRACT

There is provided an oligonucleotide sequence capable of binding to a portion of a CAstV genome, wherein the oligonucleotide sequence has binding specificity to the precapsid region of CAstV or to cDNA of the precapsid region. The oligonucleotide sequence can be one of a primer pair for use in a method for detecting the presence of CAstV in a biological sample by reverse transcription followed by amplification of the reverse transcription products using such primer pair, or a method for amplifying CAstV cDNA using such primer pair.

7 Claims, 8 Drawing Sheets

Figure 4

SEQ ID NO1: Forward

TGCGTCGAGGAGTATGCCGCTGCTGAAGAAATACAGTTACCAGAAGTCGG

SEQ ID NO 3: Reverse

GCCCGACTTCTTTCAGAAAATCTGGTAGAGGGATGGACCGAAATATAGCA

SEQ ID NO 2: Reverse

GCATGG

ORF 2 →

Table A:

| Bird | Gut content | Kidney | Liver | Pancreas | Thymus | Bursa | Spleen |
|---|---|---|---|---|---|---|---|
| 2 | 4.70 | 6.65 | 5.07 | - | 2.40 | 4.91 | 5.16 |
| 3 | 4.52 | 6.04 | 5.06 | 4.72 | 2.89 | 3.56 | 4.88 |
| 4 | 4.33 | 5.27 | 4.39 | 4.83 | 3.04 | 2.94 | 4.42 |
| 5 | 4.82 | 5.94 | 4.79 | 5.11 | 2.45 | 4.04 | 4.78 |
| Mean | 4.59 | 5.98 | 4.75 | 4.89 | 2.70 | 3.86 | 4.81 |

Figure 5

Table B.

| Sample | Age days | CAstV Log Value[a] | Sample | Age days | CAstV Log Value |
|---|---|---|---|---|---|
| VF04-01/2 | U[b] | 7.15[a] | VF07-13/9[k] | 17 | 2.75 |
| VF04-01/6 | U | 5.13 | VF08-05/8[s] | U | 5.72 |
| VF0401/11 | U | 7.44 | VF08-05/9[s] | U | 3.00 |
| VF05-01/3 | 6 | 7.41 | VF08-05/21[s] | U | 3.00 |
| VF0501/14 | 10 | 6.72 | VF08-05-24[s] | U | 2.66 |
| VF06-01/2 | 13 | 4.51 | VF08-07/2 | 10-17 | 6.45 |
| VF06-01/3 | 11 | 6.42 | 799 MO/2005 | 7 | 6.70 |
| VF06-02/1 | 25 | 3.14 | 802 AR/2005 | 7 | 3.07 |
| VF06-02/3 | 39 | Neg | 812 DE/2005 | 10 | 6.05 |
| VF06-02/9 | 42 | 4.06 | 836 NC/2005 | 8 | 6.41 |
| VF06-07/1 | 10 | 6.59 | 840 AR/2005 | 5 | 6.56 |
| VF07-04/1 | U | 2.91 | 866 GA/2006 | 14 | 4.60 |
| VF07-04/2 | U | 4.94 | 883 MO/2006 | 7 | 6.10 |
| VF07-13/1 | 14 | 6.29 | 916 CA/2006 | 12 | 5.16 |
| VF07-13/1[k] | 14 | 4.87 | 1254 GA/2008 | 7 | 7.08 |
| VF07-13/7 | 14 | 6.46 | 1255 GA/2008 | 4 | 6.45 |
| VF07-13/7[k] | 14 | 4.17 | 1335 GA/2009 | 9 | 6.25 |
| VF07-13/9 | 17 | 6.04 | 1340 GA/2009 | 9 | 4.75 |

Figure 6

Table C:

| | Day 0 | Day 5 | Day 7 | Day 14 | Day 21 | Day 28 | Day 35 | S.E.M. | P value |
|---|---|---|---|---|---|---|---|---|---|
| A CAstV gut | 0.00 $(1)^2$ | $4.44^{ab}$ (12) | $3.76^{ac}$ (12) | $2.61^d$ (11) | $5.24^b$ (12) | $3.48^{cd}$ (12) | $4.19^{ac}$ (12) | 0.323 | <0.001 |
| A CAstV kid | 0.00 (0) | 4.38 (12) | $2.79^a$ (9) | $1.90^{ab}$ (9) | $2.69^a$ (12) | $0.97^b$ (6) | $2.49^a$ (11) | 0.390 | <0.001 |
| B CAstV gut | 0.00 (0) | $5.00^a$ (12) | $3.98^b$ (12) | $4.73^a$ (12) | $3.87^{bc}$ (12) | $3.77^{bc}$ (12) | $3.26^c$ (12) | 0.221 | <0.001 |
| B CAstV kid | 0.00 (0) | $3.94^a$ (12) | $3.02^{ab}$ (11) | $2.08^{bc}$ (9) | $1.50^c$ (7) | $1.75^c$ (8) | $1.44^c$ (8) | 0.385 | <0.001 |

Figure 7

Table D:

|  | Flock A | Flock B | Flock C | Flock D | S.E.M. | P value |
|---|---|---|---|---|---|---|
| Day 4/5 CAstV gut | 4.44 | 5.00 | 5.02 | 5.06 | 0.193 | 0.091 |
| Day 4/5 CAstV kid | 4.38 | 3.94 | 4.07 | 4.65 | 0.283 | 0.295 |
| Day 7 CAstV gut | 3.76 | 3.98 | 3.94 | 4.66 | $0.261/0.239^2$ | 0.082 |
| Day 7 CAstV kid | 2.79 | 3.02 | 2.55 | 3.35 | $0.565/0.515^2$ | 0.748 |

Figure 8

Table E:

| Virus | Sample | Day 3 | Day 7 | Day 10 | Day 14 | Day 21 | Day 28 | S.E.M. | P value |
|---|---|---|---|---|---|---|---|---|---|
| CAstV | Gut | $3.04^{ab}$ $(4)^2$ | $4.23^{ac}$ (5) | $4.17^{ac}$ (5) | $4.64^c$ (5) | $1.55^b$ (1) | 0.00 (0) | 0.515 | <0.001 |
| CAstV | Kidney | 0.87 (2) | 0.00 (0) | 1.30 (2) | 1.75 (3) | 1.04 (2) | 0.00 (0) | 0.589 | 0.247 |

Figure 9

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: oligonucleotide

<400> SEQUENCE: 1
gcygctgctg aagawataca g                                           21

<210> SEQ ID NO 2
<211> LENGTH: 23
<212> TYPE: DNA
<213> ORGANISM: Artificial Sequence
<220> FEATURE:
<223> OTHER INFORMATION: oligonucleotide

<400> SEQUENCE: 2
cggtccatcc ctctaccaga ttt                                         23

<210> SEQ ID NO 3
<211> LENGTH: 25
<212> TYPE: DNA
<213> ORGANISM: Artificial Sequence
<220> FEATURE:
<223> OTHER INFORMATION: oligonucleotide

<400> SEQUENCE: 3
catccctcta ccagattttc tgaaa                                       25

<210> SEQ ID NO 4
<211> LENGTH: 20
<212> TYPE: DNA
```

```
<213> ORGANISM: Artificial Sequence
<220> FEATURE:
<223> OTHER INFORMATION: oligonucleotide

<400> SEQUENCE: 4
kcatggctyc accgyaadca                                                  20

<210> SEQ ID NO 5
<211> LENGTH: 14
<212> TYPE: DNA
<213> ORGANISM: Artificial Sequence
<220> FEATURE:
<223> OTHER INFORMATION: MGB oligonucleotide probe labelled with FAM dye

<400> SEQUENCE: 5
cagaagtcgg gccc                                                        14

<210> SEQ ID NO 6
<211> LENGTH: 18
<212> TYPE: DNA
<213> ORGANISM: Artificial Sequence
<220> FEATURE:
<223> OTHER INFORMATION: oligonucleotide

<400> SEQUENCE: 6
agcctcaaat atagagca                                                    18

<210> SEQ ID NO 7
<211> LENGTH: 22
<212> TYPE: DNA
<213> ORGANISM: Artificial Sequence
<220> FEATURE:
<223> OTHER INFORMATION: oligonucleotide

<400> SEQUENCE: 7
gatctagatg gggttttctt ag                                               22

<210> SEQ ID NO 8
<211> LENGTH: 106
<212> TYPE: DNA
<213> ORGANISM: avian astrovirus

<400> SEQUENCE: 8
tgcgtcgagg agtatgccgc tgctgaagaa atacagttac cagaagtcgg gcccgacttc      60
tttcagaaaa tctggtagag ggatggaccg aaatatagca gcatgg                    106
```

OLIGONUCLEOTIDES FOR DETECTING CHICKEN ASTROVIRUS

FIELD OF THE INVENTION

The present invention relates to improved methods of detecting nucleic acid sequences in biological samples, particularly to detect nucleic acid sequences derived from chicken astrovirus.

BACKGROUND OF THE INVENTION

Astroviruses are small, spherical, non-enveloped, positive-sense RNA viruses (28-30 nm) that cause enteric diseases in mammalian and avian species. Astroviruses of chickens have been implicated in growth depression problems, including runting stunting syndrome. Astrovirus infection is a global problem affecting broiler chicken production, which results in financial losses from increased culling, poor feed conversion and lower uniformity at slaughter with concomitant increased costs from treatment.

To date, two different astrovirus species have been detected in chickens, avian nephritis virus (ANV), and a novel astrovirus, named chicken astrovirus (CAstV). Establishing the importance of astrovirus infections in broiler growth problems has been difficult due to the absence of convenient diagnostic tests. Whilst electron microscopy (EM) can demonstrate avian astroviruses in diagnostic samples, this method relies on observing the star-like morphology which is in apparent in some types of astrovirus including ANV. In addition, EM is not suited to high sample throughput and lacks sensitivity. Isolating astroviruses in cell culture presents difficulties as they grow poorly and are often outgrown by reoviruses and adenoviruses, which also occur commonly in enteric samples. Antigen-detecting diagnostic tests including fluorescent antibody tests performed with cryostat tissue sections or tissue impression smears and antigen capture ELISA have not been developed for CAstVs due to the absence of virus-specific antisera.

A number of publications, for example WO2007/077464; Avian Dis., Vol. 50, 2006, pages 397 to 404, Pantin-Jackwood, M. J., Spackman, E., and Woolcock, P. R., "Molecular characterization and typing of Chicken and Turkey Astroviruses Circulating in the United States: Implications for Diagnostics"; Avian Dis., Vol. 51, 2007, pages 681 to 684, Day, J. M., Spackman, E., and Woolcock, P. R., "A Multiplex RT-PCR Test for the Differential Identification of Turkey Astrovirus Type 1, Turkey Astrovirus Type 2, Chicken Astrovirus, Avian Nephritis Virus and Avian Rotavirus"; and Avian Pathol., Vol. 38, 2009, pages 21 to 29, Todd, D., Smyth, V. J., Ball, N. W., Donnelly, B. M., Wylie, M., Knowles, N. J. and Adair, B. M. "Identification of Chicken enterovirus-like viruses, duck hepatitis virus type 2 and duck hepatitis virus type 3 as astroviruses" describe the use of Reverse Transcriptase Polymerase Chain Reaction (PCR) methodologies to detect enteric viruses in avians. However, generally these tests, for example as described in the publications of Pantin-Jackwood M. J et al and Todd D. et al, use primers which cannot distinguish between different avian astroviruses and therefore gene sequencing is necessary to identify particular virus types within a sample. Whilst the publication of Day J. M. et al identifies the problem that RT-PCR tests for avian astroviruses generally cannot distinguish between different astroviruses and discusses the use of a multiplex RT-PCR test to enable identification of particular virus types, this publication highlights that due to limited sequence information for virus types such RT-PCR tests may only be able to detect a limited number of viral strains within a virus type. As discussed herein, the primers determined by the present inventors provide for improved detection of CAstVs in a sample.

In the RT-PCR tests previously described, the primer pairs utilised target the RNA polymerase (ORF1B) sequence.

The detection of CAstV from avian samples is a developing field which has been limited both by the low availability of sequence information and the high degree of sequence diversity often displayed by RNA viruses. The sequence diversity observed has made it difficult to identify conserved regions on which to base the design of oligonucleotide primers for use in RT-PCR tests for the detection of CAstV. The development of a test with reliable breadth to allow universal detection of CAstV and increased sensitivity is still required.

SUMMARY OF THE INVENTION

The present invention includes nucleic acid probes and primers with binding specificity to a highly conserved region, herein defined as the "pre-capsid" region among different CAstV sequence variants which may be useful in a variety of assay formats, for example conventional RT-PCR, real-time RT-PCR and hybridisation assays. Advantageously, the nucleic acid probes and primers may allow for the highly sensitive detection of CAstV.

The region of the CAstV genome, defined herein as the "precapsid region", defined as around a 106 nucleotide region which is highly conserved and located at the end (3') of the polymerase gene of CAstV, and encompasses the 24 nucleotide intergenic region between the polymerase (ORF 1b) gene, the capsid (ORF 2) genes and 4 nucleotides of the capsid gene was selected for probe/primer design based on homology observed when several CAstV sequences were aligned using sequence identity alignment software.

Accordingly, in a first aspect, the present invention provides at least one primer of a primer pair which can be used to amplify a portion of CAstV genome, wherein the primer is an isolated oligonucleotide that has binding specificity (complements) to the precapsid region or a part thereof of CAstV or to complementary DNA synthesised by reverse transcriptase of a part of the precapsid region of CAstV. A generic avian astrovirus genome showing the locations of the ORFs and the "precapsid" region is illustrated in FIG. 1. Suitably the pre-capsid region may have a polynucleotide sequence

```
                                              (SEQ ID NO 8:)
TGCGTCGAGGAGTATGCCGCTGCTGAAGAAATACAGTTACCAGAAGT

CGGGCCCGACTTCTTTCAGAAAATCTGGTAGAGGGATGGACCGAAAT

ATAGCA GCATGG.
```

In embodiments, a primer pair of the invention can both bind to the precapsid region.

In embodiments of the invention, the at least one primer can be selected from oligonucleotide sequences comprising, consisting essentially of or consisting of:
reverse primer CGG TCC ATC CCT CTA CCA GAT TT (nt positions 68-90 in precapsid region) (SEQ ID NO: 2),
forward primer GCYGCTGCTGAAGAWATACAG (nt positions 16-36 in precapsid region) (SEQ ID NO: 1), or
reverse primer CATCCCTCTACCAGATTTTCTGAAA (nt positions 61-85 in precapsid region) (SEQ ID NO: 3).

In some embodiments, these primers are broadly useful to detect a plurality of CAstV sequence variants.

In a second aspect of the present invention there is provided a primer pair, wherein the primer pair comprises, consists essentially of or consists of oligonucleotide sequences:

```
                                        (SEQ ID NO: 1)
forward primer  GCYGCTGCTGAAGAWATACAG
and (SEQ ID NO: 3)
reverse primer  CATCCCTCTACCAGATTTTCTGAAA
or (SEQ ID NO: 2)
reverse primer  CGG TCC ATC CCT CTA CCA GAT TT
and (SEQ ID NO: 4)
forward primer  KCATGGCTYCACCGYAADCA.
```

In preferred embodiments the primer pair comprises, consists essentially of or consists of oligonucleotide sequences

```
                                        (SEQ ID NO: 1)
forward primer    GCYGCTGCTGAAGAWATACAG
and (SEQ ID NO: 3)
reverse primer    CATCCCTCTACCAGATTTTCTGAAA.
```

In a third aspect, the invention is directed to a method for detecting the presence of CAstV in a biological sample, the method comprising:
(a) performing a reverse transcription reaction, using as a template, RNA derived from the sample to produce CAstV specific reverse transcription products;
(b) amplifying the reverse transcription products, using a primer pair capable of amplifying a specific amplification product which includes a nucleic acid sequence of or which complements the precapsid region, wherein the pair comprises at least one oligonucleotide primer with binding specificity to at least a portion of the precapsid region, to produce CAstV specific amplification product, and
(c) performing a detecting step to detect the amplification product produced by the primer pair,
wherein detection of the amplification product indicates the presence of CAstV RNA in the sample.

In embodiments, the oligonucleotide sequences of the primers can both bind to the precapsid region.

In some embodiments the method comprises:
(a) performing a reverse transcription reaction using as a template RNA derived from the sample to produce CAstV specific reverse transcription products;
(b) amplifying the reverse transcription products using a primer pair wherein the pair comprises at least one oligonucleotide primer with binding specificity to at least a portion of the precapsid region, to produce CAstV specific amplification product, wherein at least one precapsid oligonucleotide primer comprises, consists essentially of or consists of an oligonucleotide sequence selected from the group:

```
                                        (SEQ ID NO: 1)
forward primer    GCYGCTGCTGAAGAWATACAG, (SEQ ID NO: 3)
reverse primer    CATCCCTCTACCAGATTTTCTGAAA,
or (SEQ ID NO: 2)
reverse primer    CGG TCC ATC CCT CTA CCA GAT TT,
```

(c) performing a detecting step to detect amplification product produced by the primer pair, wherein detection of the amplification product indicates the presence of CAstV RNA in the sample.

In embodiments the method can use a primer pair comprising, consisting essentially of or consisting of

```
                                        (SEQ ID NO: 1)
forward primer    GCYGCTGCTGAAGAWATACAG
and (SEQ ID NO: 3)
reverse primer    CATCCCTCTACCAGATTTTCTGAAA.
```

In embodiments, the method can comprise a primer pair comprising, consisting essentially of, or consisting of

```
                                        (SEQ ID NO: 2)
reverse primer    CGG TCC ATC CCT CTA CCA GAT TT
and (SEQ ID NO: 4)
forward primer    KCATGGCTYCACCGYAADCA.
```

In a fourth aspect, the present invention is directed to a method for amplifying CAstV cDNA, the method comprising:
(a) performing a polymerase chain reaction on a cDNA sample containing CAstV cDNA using a primer pair wherein the pair comprises at least one oligonucleotide primer with binding specificity to at least a portion of the precapsid region, to produce CAstV specific amplification product, and
(b) performing a detecting step to detect the amplification product, wherein detection of the amplification product indicates the presence of CAstV cDNA in the sample.

In embodiments, the oligonucleotide sequences of the primers can both bind to the precapsid region.

In some embodiments, the method comprises (a) performing a polymerase chain reaction on a cDNA sample containing CAstV cDNA using a primer pair wherein the pair comprises at least one oligonucleotide primer with binding specificity to at least a portion of the precapsid region, to produce
CAstV specific amplification product, wherein said primer comprises, consists essentially of, or consists of an oligonucleotide sequence selected from the group:

```
                                        (SEQ ID NO: 1)
forward primer    GCYGCTGCTGAAGAWATACAG, (SEQ ID NO: 2)
reverse primer    CGG TCC ATC CCT CTA CCA GAT TT,
or (SEQ ID NO: 3)
reverse primer    CATCCCTCTACCAGATTTTCTGAAA.
```

In embodiments the method can use a primer pair comprising, consisting essentially of or consisting of

```
                                        (SEQ ID NO: 1)
forward primer    GCYGCTGCTGAAGAWATACAG
and (SEQ ID NO: 3)
reverse primer    CATCCCTCTACCAGATTTTCTGAAA.
```

In embodiments the method can comprise a primer pair comprising, consisting essentially of, or consisting of

```
                                            (SEQ ID NO: 2)
reverse primer   CGG TCC ATC CCT CTA CCA GAT TT
and (SEQ ID NO: 4)
forward primer   KCATGGCTYCACCGYAADCA.
```

In some embodiments of the method, where a step of performing a reverse transcription reaction is present, the reverse transcription reaction is performed using random oligonucleotide primers. Alternatively, one or more CAstV specific reverse transcription primers may be used.

Methods for detection of amplification may include, without limitation, (a) electrophoresis, (b) capture of amplification products on a solid support to which CAstV specific probes are attached followed by quantifying bound products using an appropriate assay, for example a colourimetric assay.

In some embodiments, a method of the invention can further comprise providing at least one labelled oligonucleotide probe, which can be synthetic or naturally occurring, wherein said probe has binding specificity (for example is complementary to although not necessarily fully complementary) to a precapsid nucleotide sequence of CAstV and can form a duplexed structure with the precapsid nucleotide sequence of CAstV, and detecting the binding of such a labelled probe to a nucleic acid in a biological sample being tested.

In embodiments, the labelled probe can be selected from,

```
                              (SEQ ID NO: 5)
5'-FAM-CAGAAGTCGGGCCC-MGB.
```

Preferably the labelled probe SEQ ID NO: 5 can be used with SEQ ID NO: 1 and SEQ ID NO: 3 in real time RT-PCR.

In some embodiments, a method of the invention can comprise a step of analysing the nucleic acid in the polymerase chain reaction using melting curve analysis to detect an amplification product. The methods may also comprise a step of extracting RNA from the sample prior to the step of performing RT-PCR amplification of the sample.

According to another aspect, there is provided a kit for use in the detection of CAstV, comprising a primer pair specific for CAstV to produce CAstV-specific amplification products, the pair comprising at least one primer with binding specificity to the precapsid region and instructions for use of the primer pair.

In embodiments, the oligonucleotide sequences of the primers can both bind to the precapsid region.

In some embodiments the kit comprises at least one primer comprising, consisting essentially of or consisting of an oligonucleotide sequence selected from the group:

```
                                            (SEQ ID NO: 1)
forward primer   GCYGCTGCTGAAGAWATACAG, (SEQ ID NO: 2)
reverse primer   CGG TCC ATC CCT CTA CCA GAT TT,
or (SEQ ID NO: 3)
reverse primer   CATCCCTCTACCAGATTTTCTGAAA.
```

In preferred embodiments the kit can comprise, consist essentially of or consist of

```
                                            (SEQ ID NO: 1)
forward primer   GCYGCTGCTGAAGAWATACAG
and (SEQ ID NO: 3)
reverse primer   CATCCCTCTACCAGATTTTCTGAAA.
```

In embodiments, the kit can comprise, consist essentially of or consist of

```
                                            (SEQ ID NO: 2)
reverse primer   CGG TCC ATC CCT CTA CCA GAT TT
and (SEQ ID NO: 4)
forward primer   KCATGGCTYCACCGYAADCA.
```

The kit may additionally comprise at least one of reagents and instructions for reverse transcription, reagents for amplification, and reagents for amplified product detection. For example, the kits can contain reverse transcriptase, thermostable polymerase suitable for DNA amplification reactions, and reagents for labelling and detection of nucleic acids.

Also provided is a replication composition for use in RT-PCR, comprising a primer pair wherein the pair is capable of producing a CAstV specific amplification product, the pair comprising at least one oligonucleotide primer with binding specificity to a portion of the precapsid region to produce an amplification product, the primer comprising, consisting essentially of or consisting an oligonucleotide, selected from the group

```
                                            (SEQ ID NO: 1)
forward primer   GCYGCTGCTGAAGAWATACAG (SEQ ID NO: 2)
reverse primer   CGG TCC ATC CCT CTA CCA GAT TT,
or (SEQ ID NO: 3)
reverse primer   CATCCCTCTACCAGATTTTCTGAAA,
``` reverse transcriptase and thermostable DNA polymerase. In some embodiments, the replication composition can be in the form of a tablet, and a kit can comprise a tablet of a replication composition of the invention.

In some embodiments, primers of the instant invention or sequences derived therefrom can be useful as probes in nucleic acid hybridisation methods. This provides a further aspect of the present invention. In embodiments, a probe can comprise, consist essentially of, or consist of an oligonucleotide sequence selected from the group:

```
                                            (SEQ ID NO: 1)
forward primer   GCYGCTGCTGAAGAWATACAG, (SEQ ID NO: 2)
reverse primer   CGG TCC ATC CCT CTA CCA GAT TT,
or (SEQ ID NO: 3)
reverse primer   CATCCCTCTACCAGATTTTCTGAAA.
```

In a nucleic acid hybridisation assay, a probe, typically a single stranded nucleic acid sequence which complements a nucleic acid to be detected in a sample suspected of containing CAstV (the probe being hybridisable), is provided to the sample under conditions which allow for the hybridisation of the probe to CAstV nucleic acid in the sample. Typically a probe can have as few as 5 nucleotides. For example, in embodiments an oligonucleotide sequence of the invention can be a fragment having 5, 6, 7, 8, 9, 10, 11, 12, 13, 14, 15, 16, 17, 18, 19, 20, 21, 22, or 23 nucleotides and be capable of specifically binding to and/or amplifying the precapsid region. Only part of the probe needs to be complementary to the precapsid region of the nucleic acid sequence being detected. Further, complementarity between the probe and the nucleic acid sequence being detected need not be perfect, provided hybridisation can occur. A probe may be comprised of either RNA or DNA. The form and length of the probe will be determined by the type of hybridisation to be performed. Hybridisation methods and sample preparation to allow nucleic acid of a sample to contact the probe are known in the art. In some embodiments, a probe can be attached to a solid support, for example a nitrocellulose sheet or a dipstick, such that the immobilised probe can be brought into contact with the sample and complementary nucleic acid in the sample under conditions which allow the probe and complementary nucleic acid to hybridise to each other. A labelled probe, for example a nucleic acid complementary to a second and different region of the complementary nucleic acid in the sample provided with a detectable label, for example a probe including a radioactive moiety, a fluorescent moiety or a moiety to which an antibody can bind may then be applied to the solid support and binding of the labelled probe can be suitably detected.

The primers and/or probes of the invention can be prepared using conventional methods, for example DNA can be chemically synthesised. Suitably, the primers and/or probes may be modified by means known in the art, for example, they may include nucleotide analogs, they may be methylated, they may be covalently bound to proteins, antibodies, signal peptides, labels capable of providing a detectable signal, include chelators or have modified backbone linkages.

DETAILED DESCRIPTION OF THE INVENTION

In this disclosure, a number of terms and abbreviations are used. The following definitions are provided:
"Polymerase Chain Reaction" is abbreviated PCR.
"Reverse transcription followed by polymerase chain reaction" is abbreviated RT-PCR. This refers to the sensitive technique for qualitative or quantitative analysis of for example template polynucleotide sequences or gene expression and signal amplification in in situ hybridisations. The technique consists of synthesis of cDNA from RNA by reverse transcription (RT), and amplification of a specific cDNA by polymerase chain reaction (PCR). Reverse transcriptase is a RNA dependent DNA polymerase that catalyses the polymerization of nucleotides using template RNA, or RNA:DNA hybrids.
"Chicken Astrovirus" is abbreviated CAstV.

The term "isolated" refers to materials, such as nucleic acid molecules, which are substantially free or otherwise removed from components that normally accompany or interact with the materials in a naturally occurring environment. An isolated nucleic acid typically contains less than about 50%, preferably less than about 75%, and most preferably less than about 90% of the components with which it was originally associated.

The terms "polynucleotide", "polynucleotide sequence", "oligonucleotide" and "nucleic acid sequence" are used interchangeably herein wherein the surrounding context provides for this. A "oligonucleotide" as used herein refers to purine- and pyrimidine-containing polymers of any length, either polyribonucleotides or polydeoxyribonucleotides, which can be single or double stranded, such as, for example, DNA-DNA, DNA-RNA and RNA-RNA. An oligonucleotide may optionally contain synthetic, non-natural or altered nucleotide bases. A polynucleotide in the form of a polymer of DNA may be comprised of one or more strands of cDNA, genomic DNA, synthetic DNA, or mixtures thereof.

Binding specificity is where an oligonucleotide can hybridise to or can complement a nucleic acid sequence of the precapsid region of CAstV in preference to another nucleic acid sequence. For example where the oligonucleotide sequence of the invention has template specificity and can bind to the precapsid region (sample template sequence) in preference to "background nucleic acid, for example nucleic acid other than sample template which may or may not be present in a sample.

As used herein, the term "probe" refers to an oligonucleotide (i.e., a sequence of nucleotides), which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

A "complement" of a nucleic acid sequence as used herein refers to the antisense sequence that participates in Watson-Crick base-pairing with another nucleic acid sequence and which can hybridize to the other nucleic acid sequence under appropriate conditions of temperature and ionic strength. A nucleic acid molecule is hybridisable to another nucleic acid molecule when a single strand form of the nucleic acid molecule can anneal to the other nucleic acid molecule under appropriate conditions of temperature and ionic strength. Hybridisation as discussed herein refers to the binding, duplexing, or hybridising of a molecule to a particular nucleotide sequence under stringent conditions when that sequence is present in a complex mixture (e.g., total cellular) DNA or RNA. Stringent hybridisation occurs when a nucleic acid binds a target nucleic acid with minimal background. Typically, to achieve stringent hybridisation, temperatures of around 1° C. to about 20° C., more preferably 5° C. to about 20° C. below the Tm (melting temperature at which half the molecules dissociate from their partner) are used. However, it is further defined by ionic strength and pH of the solution. An example of a highly stringent wash condition is 0.15 M NaCl at 72° C. for about 15 minutes. An example of a stringent wash condition is a 0.2× sodium chloride and sodium citrate (SSC) wash at 65° C. for about 15 minutes (see, Sambrook and Russell, infra, for a description of SSC buffer for example 20×SSC made by dissolving 175.3 g of NaCl and 88.9 g of sodium citrate in 800 ml distilled water. Adjusting pH to pH7.0 with HCl (1 M) and adjusting volume to 1 L with distilled water.). Often, a high stringency wash is preceded by a low stringency wash to remove background probe signal. An example of a medium stringency wash for a duplex of, for example, more than 100 nucleotides, is 1×SSC at 45° C. for 15 minutes. An example of a low stringency wash for a duplex of for example more than 100 nucleotides, is 4-6×SSC at 40° C. for 15 minutes. For short probes (for example about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (for example, >50 nucleotides). Hybridisation requires that the two nucleic acids contain complementary sequences, although depending on the stringency of the hybridisation, mismatches between bases are possible. The term "primer" refers to an isolated oligonucleotide of between about 5 to 50 nucleotides in length, preferably between about 10 to 50, more preferably 12 to 25 nucleotides in length and most preferably between about 12 and 18 nucleotides in length, that forms a duplex with a single stranded nucleic acid sequence of interest (complementary strand), and which is capable of acting as a point of initiation of nucleic acid synthesis to allow for polymerization of a complementary strand using a polymerase. The primer must be sufficiently long to prime the synthesis of extension products in the presence of the inducing agent. The exact lengths of the primers will depend on many factors, including temperature, source of primer and the use of the method. As used herein, the term "primer" refers to an oligonucleotide which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide.

Herein, the term "precapsid" region" defines a nucleotide sequence of 106 nt, which is highly conserved and located at the end (3') of the polymerase gene, and includes the intergenic region between the polymerase gene (orf 1b) and the capsid gene (orf 2) and the first 4 nucleotides of the capsid gene. The precapsid region ends with the first four bases of ORF 2 (~2.2 Kb upstream from the poly A tail) and extends upstream encompassing the 24 bp intergenic region between ORFs 1b and 2 and 78 bp from the 3' region of ORF 1b.

By "consisting essentially of" it is meant that an oligonucleotide, whilst not identical to the oligonucleotide presented herein, does not include additional, substituted or deleted nucleotide(s) to an oligonucleotide sequence of the invention described herein which significantly alters the character of the olignonucleotide sequence of the invention such that it cannot complement a portion of the precapsid region.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness. Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

The present inventors have determined that detection of CAstV in a biological sample is more efficient when oligonucleotides having sequences complementary to precapsid sequences present in the CAstV RNA are used as probes or primers for amplification. Oligonucleotide primers can be selected based on theoretical considerations of sequences conservation, intra- and inter-molecular interactions, predicted secondary structure of the region to be amplified and the surrounding sequence. Advantageously methods of the invention can be used to test field samples from broiler flocks with growth problems and from longitudinal surveys of commercial flocks.

Accordingly, a biological sample can be obtained from a subject by any conventional means and tested according to the methods of the invention. Suitably a biological sample may include a sample from an avian, for example a chicken. The sample, including nucleic acid to be tested, may be obtained from feathers, blood, faeces, the intestines and gut or intestinal contents, eggs including dead in shell embryos, or tissues where the virus replicates including kidney, liver, pancreas, spleen or the like from an avian. Suitably, for example, when the sample is faeces and/or gut contents, crude virus suspensions may be prepared as 10% homogenates in phosphate buffered saline (PBS). These may be clarified using 3000 g for 30 minutes and an aliquot (e.g. 200 microliter) of clarified extract can be extracted. With swabs, suspensions in 1-2 ml PBS may be made and clarified as above prior to extraction/analyses. With tissues such as the kidney, 10% tissue homogenates may be prepared in PBS, and be used clarified as above or remain unclarified prior to extraction/analyses. Homogenates (10% in PBS) can also be prepared from early dead whole embryos (days 1-5 post incubation) or tissues including kidney, liver and intestines recovered from late-dead embryos, and be clarified as above or remain unclarified prior to extraction/analyses. A number of commercial kits are available to extract RNA from tissue samples. These are well known to those skilled in the art, for example QIAamp Viral RNA Mini Kit (Qiagen, Crawley, UK).

The sample can then be subjected to reverse transcription using (a) random primers or (b) reverse precapsid oligonucleotide primers specific for CAstV Following the reverse transcription reaction the products are amplified. Any suitable method of amplification may be used, including iterative processes such as, but not limited to polymerase chain reaction (PCR), ligase chain reaction, strand displacement amplification, transcription mediated amplification and nucleic acid single base amplification. Preferably, PCR is used. Amplification is performed at conditions specified by the primer pair used. In some embodiments a reaction mixture containing all the necessary components may be added to the reverse transcription reaction. Alternatively, a replication composition of the invention may be used.

The present inventors have determined that certain pairs of primers are particularly advantageous in detecting CAstV in subject samples. Non-limiting examples of useful primers are listed in table 1.

TABLE 1

| Primer | Sequence | SEQ ID NO: |
|---|---|---|
| forward primer | GCYGCTGCTGAAGAWATACAG | SEQ ID NO: 1 |
| forward primer (binds upstream from precapsid region in ORF 1b, as used in the conventional RT-PCR | KCATGGCTYCACCGYAADCA | SEQ ID NO: 4 |

TABLE 1-continued

| Primer | Sequence | SEQ ID NO: |
|---|---|---|
| generating ~510 bp product) | | |
| reverse primer | CGG TCC ATC CCT CTA CCA GAT TT | SEQ ID NO: 2 |
| reverse primer | CATCCCTCTACCAGATTTTCTG-AAA | SEQ ID NO: 3 |

Preferred pairs of primers which may be used are:

```
                                            (SEQ ID NO: 1)
  forward primer   GCYGCTGCTGAAGAWATACAG
  and (SEQ ID NO: 3)
  reverse primer   CATCCCTCTACCAGATTTTCTGAAA, (SEQ ID NO: 2)
  reverse primer   CGG TCC ATC CCT CTA CCA GAT TT
  and (SEQ ID NO: 4)
  forward primer   KCATGGCTYCACCGYAADCA.
```

In a particularly preferred embodiment, the pair of primers used comprise, consist essentially of or consist of:

```
                                            (SEQ ID NO: 1)
  forward primer GCYGCTGCTGAAGAWATACAG
  and (SEQ ID NO: 3)
  reverse primer CATCCCTCTACCAGATTTTCTGAAA.
```

This particular primer pair can advantageously be used with a Taqman probe as the pair amplify a very small product of around 70 nucleotides.

Following amplification, the amplified products may be detected by any method known in the art, including, for example, without limitation, gel electrophoresis, fluorescence or chemiluminescence.

Real time primer directed nucleic acid amplifications (real time PCR and real time RT-PCR) may be performed using primer pairs of the instant invention. Examples of suitable "real time" methods are set forth in U.S. Pat. Nos. 6,171,785 and 5,994,056.

BRIEF DESCRIPTION OF THE FIGURES

Embodiments of the present invention will now be described by way of example only with reference to the accompanying figures in which:

FIG. 4 shows the sequence of the 106 nt "precapsid" region, encompassing 78 nt of ORF 1b, 24 nt intergenic region and first 4 nt of ORF 2 (shown by arrow). The locations of the forward (SEQ ID NO: 1) and reverse (SEQ ID NO: 3) primers used for the real time RT-PCR are indicated (shaded boxes). The location of the reverse primer (SEQ ID NO: 2) used in the conventional RT-PCR test that amplifies a 510 bp product is also shown (underlined bold).

FIG. 5 shows table A which describes real-time RT-PCR detection of CAstV RNA in tissues from experimentally infected chickens. One-day-old SPF chickens were infected with the FP3 isolate of CAstV and tissue extracts from 4 chickens were tested at 7 days post infection. Virus RNA copy numbers are shown as their logarithm values (to the base 10).

FIG. 6 shows table B which describes real-time RT-PCR detection of CAstV RNA in field samples wherein a: Log values relate to the virus RNA copy numbers expressed as logarithmic values (to the base 10). b: U indicates that the age of the bird sampled is unknown and all samples are from gut contents with exception of those marked with "k", which are from kidney, and those marked "s", which are from cloacal swabs.

FIG. 7 shows table C which describes real-time RT-PCR detection of CAstV RNA in gut content and kidney samples collected in longitudinal surveys of flocks A and B[1]. Virus RNA copy numbers are shown as their logarithm values (to the base 10). Within a row, means with a common superscript are not significantly different. The day 0 values were not considered in the one-way analysis of variance. The figures in parentheses are the numbers of samples (of 12 tested) that were positive for virus RNA.

FIG. 8 shows table D which describes real-time RT-PCR detection of CAstV RNAs in gut content and kidney samples collected at early timepoints from four broiler flocks different performance values.[1] Virus RNA copy numbers are shown as their logarithm values (to the base 10). Within a row, means with a common superscript are not significantly different. S.E.M. presented is for min/max replication as the number of birds from each flock differs FIG. 9 shows table E which describes real-time RT-PCR detection of CAstV RNAs in gut content and kidney samples collected from experimentally infected broiler chickens (infected at day 0) at selected times post infection.[1] Virus RNA copy numbers are shown as their logarithm values (to the base 10) Within a row, means with a common superscript are not significantly different. The figures in parentheses are the numbers of samples (of 5 tested) that were positive for virus RNA.

EXAMPLES

RT-PCR Test for all Chicken Astroviruses

Based on partial genome sequences of CAstV fragments that were amplified from field samples collected from growth problem chickens a region of around 106 nt, which is highly conserved and encompasses 78 nt at the 3' end of the polymerase gene, the 24 nt intergenic region between the polymerase gene (ORF 1b) and the capsid gene (ORF 2) and 4 nt at the start of the capsid gene, has been identified. Herein, this highly conserved region has been referred to as the "precapsid" region. This region shows high levels of conservation when "different" CAstVs are compared.

Sample Preparation

Intestinal contents or cloacal swabs were sampled from chickens collected from problem flocks in the UK and Germany and stored at −80° C. Swabs were immersed in 0.5 ml of chilled phosphate buffered saline (PBS) and vortexed thoroughly. The swab suspensions underwent one freeze/thaw cycle at −80° C. before the swab was removed. Intestinal contents were diluted 1:10 in chilled PBS and then shaken by hand briefly with glass beads to disrupt the solid material. Both suspensions were centrifuged at 3000×g at 4° C. for 30 min, and the supernatants transferred to fresh tubes for storage at −80° C. until required.

RNA Extraction

Viral RNA was extracted from 140 μl of each supernatant using the QIAamp Viral RNA Mini Kit (Qiagen, Crawley, UK) according to the manufacturer's instructions. Each RNA was eluted in 30 μl of RNase-free water.

RT-PCR Amplification

A pair of primers was designed to amplify a 510 bp product from CAstVs. The degenerate forward primer, CAstV-for KCA TGG CTY CAC CGY AAD CA (SEQ ID NO: 4) was located within ORF 1b while the non-degenerate reverse primer CAstV-rev CGG TCC ATC CCT CTA CCA GAT TT (SEQ ID NO: 2) was located in a conserved region located close to the junction of ORF 1b and ORF 2 described herein as the "precapsid region". One-step RT-PCR was performed on the RNAs using the above primers and the SuperScript III One-Step RT-PCR System with Platinum® Tag DNA Polymerase kit (Invitrogen, Paisley, UK). Each reaction contained 1× reaction buffer, 1 μM of each primer, 1 μl of enzyme mix, 2.5 μl RNA and diethyl pyrocarbonate (DEPC)-treated $H_2O$ to 25 μl. Amplification occurred in a Veriti thermocycler (Applied Biosystems, Warrington, UK) starting with a reverse transcription step of 45° C. for 30 min, then an initial denaturing step of 95° C. for 2 min, followed by 40 cycles of denaturation at 95° C. for 30 sec, annealing at 59° C. for 30 sec and extension at 68° C. for 30 sec. There was a final extension step at 68° C. for 7 min. The CAS pol 1F and CAS pol 1R primers, part of a multiplex RT-PCR assay for detecting CAstV (Avian Pathol., Vol. 38, 2009, pages 21 to 29, Todd, D., Smyth, V. J., Ball, N. W., Donnelly, B. M., Wylie, M., Knowles, N.J. and Adair, B. M. "Identification of Chicken enterovirus-like viruses, duck hepatitis virus type 2 and duck hepatitis virus type 3 as astroviruses") were used in one-step RT-PCR as above with a 55° C. annealing temperature and an extension step of 1 min per cycle. The CAS poll F and CAS poll R primers were originally described and used in the Day et al (2007) paper and were used as comparative primers.

Detection of PCR Products

The PCR products were electrophoresed at 125 V for 40 min on a 1% agarose gel in 1×Tris-acetate EDTA (TAE) buffer and were visualised by ethidium bromide staining and ultraviolet (UV) transillumination. Amplicons of 510 bp were excised from the gel and purified using the Wizard SV Gel and PCR Clean-Up System (Promega, Southampton, UK). Twenty of the purified PCR products were sequenced in both directions using the same forward and reverse primers used to generate them and the Big Dye® Terminator v3.1 Cycle Sequencing Kit (Applied Biosystems). The products were sequenced commercially. Sequencing data was analysed using the Vector NTI suite (Invitrogen). Phylogenetic analysis was conducted on trimmed amplicons of 458 nucleotide using MEGA version 4. This confirmed that amplicons were CAstV specific.

Previously described degenerate avian astrovirus primers that amplify a 434 bp fragment from within the pol gene of a wide range of avian astroviruses were used in one-step RT-PCR to verify the presence of specific astroviruses in ANV, DHV-2 and DHV-3 isolates (Todd, D., Smyth, V. J., Ball, N. W., Donnelly, B. M., Wylie, M., Knowles, N. J. & Adair, B. (2009). Identification of chicken enterovirus-like viruses, duck hepatitis virus (DHV) type 2 and DHV type 3 as astroviruses. Avian Pathology 38, 21-29). These amplicons were electrophoresed, gel excised, purified and sequenced as described above.

Determination of Assay Sensitivity

An RT-PCR product of 858 bp, derived from a CAstV isolate, was cloned into the pCR®II-TOPO vector (Invitrogen). The RT-PCR product amplified by the forward primer (5'-AGC CTC AAA TAT AGA GCA G-3') (SEQ ID NO: 6) and reverse primer (5'-GAT CTA GAT GGG GTT TTC TTA G-3') (SEQ ID NO: 7) contained regions of ORF 1b and ORF 2. The vector construct was linearised by Xho1 digestion and in vitro transcribed from the SP6 promoter using the MEGAscript®SP6 kit (Ambion, Warrington, UK), according to the manufacturer's instructions, but with an overnight incubation period at 37° C. Following transcription, the in vitro transcribed RNA was treated with Turbo DNase (Ambion) and then further purified from template contamination by TRIzol (Invitrogen) extraction. The quality of the in vitro transcribed RNA was assessed by RT-PCR and its purity by PCR using the CAstV-for and -rev primers and the cycling conditions above (excluding the RT step).

The concentration of the in vitro transcribed RNA was determined using a Genova spectrophotometer (Jenway, Dunmow, UK). The minimum amount of RNA that could be detected by the assay was determined by performing the CAstV RT-PCR on 10-fold serial dilutions of the in vitro transcribed RNA. The products were visualised under UV transillumination after electrophoresis on a 1% agarose gel stained with ethidium bromide in 1×TAE buffer. The gene copy limit of detection (LOD) was then calculated for the last dilution visible on the gel.

Longitudinal Surveys

Four flocks were screened for the presence of CAstV using RT-PCR based on the CAstV-for and -rev primers SEQ ID NO: 2 and 4. These flocks were from different sites belonging to the same UK poultry organisation and, based on recent performances, were predicted to exhibit average and below average performances. Gut contents from .about.12 birds were sampled from each flock at each of 10 timepoints ranging from day 0 to day 42. The 12 samples were grouped into 4 pools and processed as described above. The performance of each flock was estimated after slaughter by calculating European production efficiency factor (EPEF) values, which represent standard measures of overall flock performance as determined by the equation:

$$EPEF = \frac{liveweight(\text{kg}) \times liveability(\%)}{\text{age at depletion (days)} \times \text{feed conversion rate}} \times 100$$

Detection Limit of CAstV RT-PCR Test

The limit of detection (LOD) of the RT-PCR assay was determined using RNA that had been in vitro transcribed from the recombinant plasmid containing an 858 bp insert. The last 10-fold serial dilution with which a visible RT-PCR product was amplified corresponded to approximately 60 molecules of the viral RNA target (data not shown).

Specificity and Performance of CAstV RT-PCR Tests

The performance of the RT-PCR tests based on CAstV-for and -rev primers of the present invention (SEQ ID NO: 2 and 4) and the CAS pol 1F and CAS pol 1R primers, used by Ayman Dis., Vol. 51, 2007, pages 681 to 684, Day, J. M., Spackman, E., and Woolcock, P. R., "A Multiplex RT-PCR Test for the Differential Identification of Turkey Astrovirus Type 1, Turkey Astrovirus Type 2, Chicken Astrovirus, Avian Nephritis Virus and Avian Rotavirus" were compared using representative isolates of CAstV. Fragments of 510 bp were amplified from reference CAstV isolates using the CAstV-for and -rev primers.

Using the CAS pol 1F and CAS pol 1R primer set, although strongly stained RT-PCR products of 362 bp were generated with the 612 and reference CAstV isolates, very weak signals were obtained using the 11522 and 1009 isolates, and no products were generated from the 11672 and FP3 isolates.

The specificity of the RT-PCR test, based on the CAstV-for and -rev primers SEQ ID NO: 2 and 4, was evaluated using RNAs extracted from ANV, duck hepatitis virus type 2 (DHV-2) and type 3 (DHV-3) isolates. Astrovirus-specific fragments of 434 bp were amplified from these RNAs using RT-PCR based on degenerate primers previously described in Avian Pathol., Vol 38, 2009, pages 21 to 29, Todd, D., et al. However, no amplicons were produced with these RNAs using RT-PCR based on the CAstV-for and -rev primers.

Detection of CAstVs in Field Samples

Figure 3:
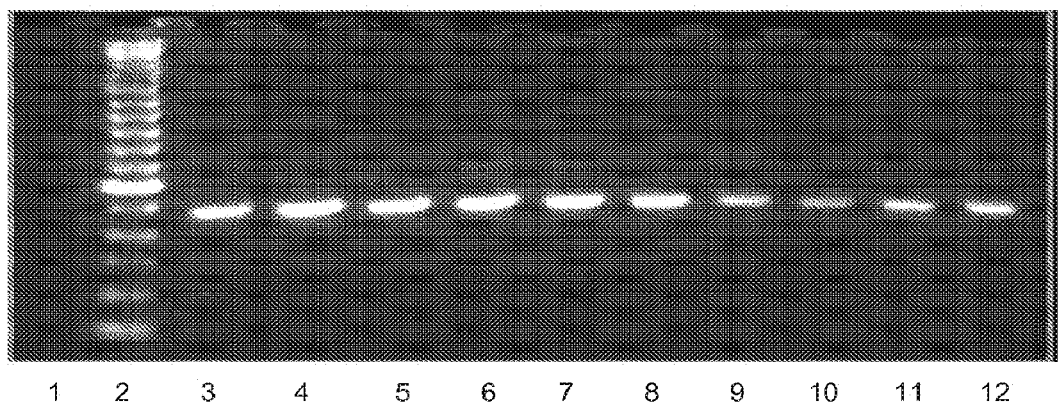
FIG. 3 shows analysis of reaction products of RT-PCR by agarose gel electrophoresisis followed by ethidium bromide staining and UV transillumination that DNA amplicons of ~510 bp were clearly visible in 50 of the 52 (96%) field samples tested wherein Lane 1 is negative control; lane 2 is molecular weight marker; lanes 3 to 12 are amplicons generated with different biological samples tested.

The RT-PCR test based on the CAstV-for and -rev primers SEQ ID NO: 2 and 4 was applied to RNAs that had been extracted from field samples. These were obtained from broiler flocks with enteritis and growth retardation problems and included 39 gut content and 10 swab samples collected from 10 outbreaks that occurred in 5 UK poultry organisations from October 2004 to March 2008. Where known, the birds sampled were aged from 4 to 42 days. Three field samples submitted from problem flocks in Germany from 2004 to 2006 were also investigated. Analysis of the reaction products by agarose gel electrophoresisis followed by ethidium bromide staining and UV transillumination showed that DNA amplicons of ~510 bp were clearly visible in 50 of the 52 (96%) field samples tested. In most cases, and with the exception of the primer band, no other DNA bands were visible (FIG. 3). When the RT-PCR test based on the CAS pol 1F and CAS pol 1R primers was applied to the same 52 field samples, 30 (58%) produced amplicons.

Detection of CAstVs in Longitudinal Survey Samples

CAstVs were detected by RT-PCR using the CAstV-for and -rev primers SEQ ID NO: 2 and 4 in pooled gut content samples from the 4 broiler flocks at time points ranging from day 4 to day 42, but all samples were negative for CAstV at day 0. Flocks A and C were CAstV-negative at half of the timepoints, with CAstV being detected in 33.3% and 30.0% of the samples in flocks A and C respectively. With flocks B and D, CAstVs were detected at more timepoints (flock B, 8; flock D, 9) and in higher numbers of pooled samples (flock B, 72.5%; flock D, 67.5%). Highest CAstV detection levels across all flocks occurred in samples at days 4 or 5 (14/16; 87.5%), day 7 (12/16; 75%) and day 35 (12/16; 75%). The 3 male flocks had EPEF flock performance values of 327 (flock A), 315 (flock C) and 308 (flock B), while flock D, a female flock, had an EPEF value of 238.

The high sensitivity of the methods described herein, which has an estimated LOD of approximately 60 genome copies, is reflected by the successful detection of CAstV RNA in 50/52 (96%) field samples from broiler flocks with enteritis and growth retardation problems and in 6/6 CAstV isolates that can be propagated in vitro.

The test represents an improvement on the test described previously by Day, J. M., et al., which, while having a similar estimated LOD, failed to detect CAstVs in 22/52 (42%) field samples and swabs, 50 of which were positive using the newly-described test.

The availability of an RT-PCR test that can sensitively detect CAstVs provides a useful diagnostic tool with which to begin investigations into CAstV epidemiology and pathogenicity.

Real-Time RT-PCR

The severity of the pathogenic effects caused by particular CAstV infections may well correlate with the extent of virus replication in the intestine or in other internal organs such as kidney that is known to be infected by some CAstVs. The inventors have developed a real-time quantitative reverse transcriptase-polymerase chain reaction (RT-PCR) assay using a TaqMan®hdrolysis probe (SEQ ID NO: 5) in a single tube procedure for rapid detection of chicken astrovirus (CAstV). The assay uses oligonucleotides SEQ ID NO: 1 and SEQ ID NO: 3 to generate an amplicon of 70 bp located within the 3' region of ORF 1b and the intergenic region between ORF 1b and ORF 2. It has a limit of detection (LOD) of ~105 template copies per reaction using an in vitro transcribed RNA of 858 bp.

The majority of samples from growth-retarded chickens were positive and included gut contents, faecal matter, organ homogenates and swabs. Moreover, no PCR inhibition was observed for any of the sample types. Furthermore, the assay was tested with gut contents, kidneys, liver, pancreas, thymus, bursa of Fabricius and spleen of birds 7 days after being experimentally inoculated with the CAstVFP3 isolate and the kidney was found to contain the highest level of CAstV and may prove useful for diagnostic purposes.

The real-time RT-PCR assay described can be used to rapidly diagnose CAstV infections, being extremely sensitive and specific and can be used to quantitate viral genomic RNA in clinical samples.

Sample Preparation

Swab samples and gut contents were processed as described previously. Faecal matter was processed in the same manner as gut contents. Tissue samples were ground in a mortar and pestle and diluted 1:10 in chilled phosphate buffered saline (PBS) containing amp B and strong antibiotics. The tissue homogenates were clarified by centrifugation at 4500×g for 30 min at 4° C. and the supernatants retained for RNA extraction.

RNA Extraction

Viral RNA was extracted from 140 μl of each supernatant using the QIAamp Viral RNA Mini Kit (Qiagen, Crawley, UK) according to the manufacturer's instructions. Each RNA was eluted in 40 μl of RNase-free water.

Real-Time RT-PCR Assay

Figure 1:
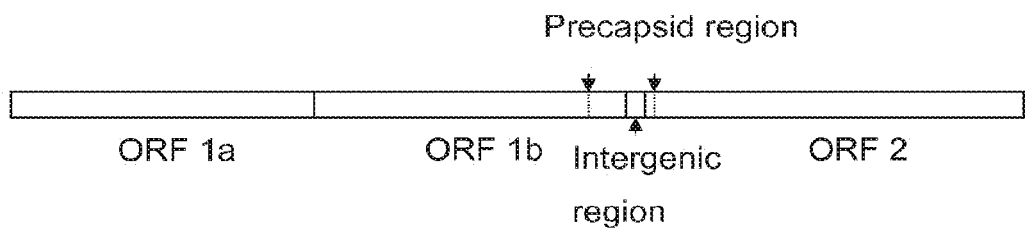
FIG. 1 shows an illustration of the avian astrovirus genome, showing the locations of ORF 1a (viral protease), ORF 1b (polymerase) and ORF 2 (capsid). The location of the precapsid region, which encompasses the intergenic region (between ORF 1b and ORF 2), is also shown.
Figure 2:
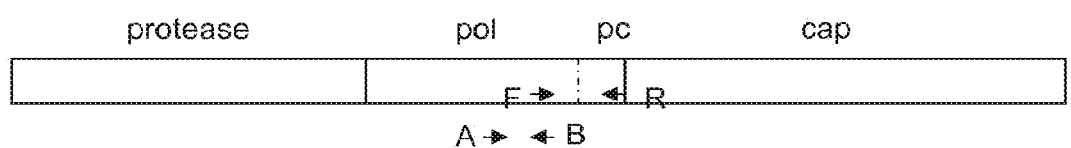
FIG. 2 shows a diagrammatic representation of the putative chicken astrovirus genome showing the approximate locations of the CAstV forward (F) and CAstV reverse (R) primers (SEQ ID NO: 4 and 2 respectively) and CAS pol 1F (A) and CAS pol 1R (B) primers. Pol denotes the polymerase gene; pc denotes the precapsid region and cap denotes the capsid gene.

Primers SEQ ID NO: 1 and SEQ ID NO: 3 and a TaqMan® labeled probe SEQ ID NO: 5 with non-fluorescent minor groove binder (MGB) were designed manually using the Primer Express® software version 3.0 (Applied Biosystems, Warrington, UK) to complement the polynucleotide sequence of the precapsid region of 106 nt, which comprises the 3'end of ORF1b and the 24 nt intergenic region between ORF1b and ORF2 and the first 4 nt of ORF 2 (FIG. 1). The probe was designed to hybridise to the same strand as the forward primer.

The sequences of the assay components are:

Forward primer, GCYGCTGCTGAAGAWATACAG - SEQ ID NO: 1

Probe, 5'-FAM-CAGAAGTCGGGCCC-MGB - SEQ ID NO: 5

Reverse primer, CATCCCTCTACCAGATTTTCTGAAA.-. SEQ ID NO: 3

The primers and probe were synthesised by Applied Biosystems. Real-time RT-PCR reactions were set up in triplicate per sample with a total volume of 20 µl per replicate reaction. Each reaction comprised 10 µl of AgPath-ID™One-step RT-PCR 2× buffer (Applied Biosystems), 0.8 µl AgPath-ID™One-step RT-PCR enzyme (Applied Biosystems), primers to a final concentration of 400 nM, probe to a final concentration of 120 nM, 2 µl RNA and nuclease-free dH$_2$O to 20 µl. The reaction was conducted in a 7500 Real-Time PCR System (Applied Biosystems) starting with an initial reverse transcription stage at 45° C. for 10 min, then an initial denaturation stage at 95° C. for 10 mins, followed by 40 cycles of denaturation at 95° C. for 15 sec and primer annealing and amplification at 60° C. for 45 sec. Fluorescence readings were taken during the amplification stage. During post PCR analysis, cycle thresholds were set while the reactions were in true exponential phase prior to the linear phase.

Determination of Assay Sensitivity, Efficiency and Specificity

To determine the sensitivity of the assay, a PCR product of 858 bp, derived from a CAstV isolate, was cloned into the pCR®II-TOPO vector (Invitrogen, Paisley, UK). Run-off RNA transcripts were produced and quantified as described previously. Ten-fold serial dilutions of the in vitro transcribed RNAs were made and examined in triplicate by real-time RT-PCR as described above. The assay's limit of detection (LOD) was determined from the last dilution to give a positive amplification. The assay's PCR efficiency was also determined from the ten-fold dilution series of in vitro transcribed RNA using the equation, Efficiency=$10^{(-1/slope)}-1$. The specificity of the assay to CAstV was tested using field samples previously shown to be positive for CAstV by RT-PCR. A CAstV real-time RT-PCR amplicon was cloned and sequenced to ensure specificity. The CAstV real-time PCR assay was also tested against duck astroviruses, DHV-2 and DHV-3, and ANV.

Assay Evaluation

The performance of the assay was assessed for PCR inhibition against RNAs from different sample types including gut contents, swabs, faecal matter and organ homogenates using the TaqMan® Exogenous Internal Positive Control (Exo IPC) Reagents kit (Applied Biosystems). This one-tube end point analysis approach duplexes the FAM-labeled CAstV assay with the VIC-labeled Exo IPC assay. The Exo IPC assay is at a lower concentration than the CAstV assay and fluorescence readings are taken both during the amplification stages and at the end of the cycling in a final extension phase. The real-time PCR reactions were performed in triplicate per sample with a total volume of 20 µl per replicate reaction. Each reaction comprised 10 µl of AgPath-ID™One-step RT-PCR 2× buffer (Applied Biosystems), 0.8 µl AgPath-ID™One-step RT-PCR enzyme (Applied Biosystems), CAstV primers to a final concentration of 900 nM, CAstV probe to a final concentration of 200 nM, 2 µl of 10×Exo IPC mix, 0.4 µl of 50×Exo IPC DNA, 2 µl of RNA or nuclease-free dH$_2$O (no template control) or 10×Exo IPC Block (no amplification control) and nuclease-free dH$_2$O to 20 µl. The cycling and detection conditions were identical to the above method but ended with a final extension hold and fluorescence reading at 60° C. for 1 min.

Sensitivity, Efficiency and Specificity of Real-Time Assay

The detection limit and efficiency of the CAstV real-time RT-PCR assay were determined using $C_T$ values obtained from a ten-fold dilution series of run-off RNAs, which had been in vitro transcribed from a cloned CAstV11672 PCR product of 858 bp. An LOD of approximately 105 copies was estimated for the assay, based on the last reproducibly detectable dilution, which had a $C_T$ value of ~35. A standard curve of the $C_T$ values versus the RNA dilutions was constructed for the assay, and this was used to estimate the number of viral RNA copies in unknown samples. For convenience, the viral RNA copy numbers were transformed to their logarithm (to the base 10) values, hereafter termed "log values". The PCR amplification efficiency of the assay was also estimated from the slopes generated from the same dilution series using the equation, Efficiency=$[10^{(-1/slope)}-1]\times100$. This was estimated to be 97.98% for the CAstV assay. The $R^2$ value was 0.999. Appropriate dilutions of viral RNA, which was extracted from cell culture grown pools of CAstV11672, was used as positive control samples in all rRT-PCR experiments. A $10^{-3}$ dilution of CAstV11672 RNA extract produced a $C_T$ value of 29 (+/−0.5). When the TaqMan® Exo IPC assay was applied to RNA extracts from 20 randomly selected gut content samples, no PCR inhibition was observed for any of the samples. Standard curves of the $C_T$ values versus the RNA dilutions were constructed and used to estimate the number of viral copies in unknown samples. For convenience, the viral copy numbers were transformed into logarithm values, hereafter termed "log values".

Assay Specificity

The CAstV real-time RT-PCR test was positive for all 5 CAstV isolates with a maximal log value of 8.23 being obtained with RNA extracted from an undiluted sample of CAstV612 that had been grown in chorioallantoic membranes of embryonated chicken eggs. The CAstV assay was negative when applied to ANV-1, DHV-2 and DHV-3 virus samples. An amplicon of CAstV was cloned and sequenced using the M13 forward and reverse primers and found to have sequences specific to their respective viruses.

Detection of CAstV RNAs in Tissues from Experimentally-Infected Chickens

The assay was further tested on gut contents, kidney, liver, pancreas, thymus, bursa and spleen taken from SPF chicks 7 days after being experimentally infected with CAstVFP3 (Table A). At 7 days p.i., the kidneys were shown to be the most heavily infected tissue with log values ranging from 5.27 to 6.65 (mean 5.98). Gut content, liver, pancreas and spleen had similar mean log values of 4.59, 4.75, 4.89 and 4.81 respectively, while the lymphoid tissues, bursa of Fabricius and thymus, had mean log values of 3.86 and 2.70 respectively.

Detection of CAstV RNAs in Diagnostic Samples from Broiler Flocks.

The CAstV assay was assessed using RNAs extracted from a panel of 36 field samples that originated in the UK and USA (Table B). These comprised samples prepared from gut contents (n=29), kidneys (n=3) and cloacal swabs (n=4). The majority (27 of 29) of the gut content samples came from broiler flocks with enteritis and/or growth retardation problems. For the CAstV assay, 35/36 field samples tested positive with log values ranging from 2.66 to 7.44. Eighteen of 27 (66.7%) gut content samples from growth-retarded broilers were considered to have high (>5.99) log values, while 2 samples (7.4%) had comparatively low (<4.00) log values.

One of the 2 samples from a healthy pedigree flock was negative (VF06-02/3) and the other had a low log value of 3.14 (VF06-02/1). The CAstV RNA log values for the 3 kidney samples ranged from 2.75 to 4.87 and were less than their counterpart gut content samples (range 6.04-6.46). None of the swab samples, two of which were from broilers with "wet litter" had high log values.

Detection of CAstV RNA in Longitudinal Survey Samples of Broiler Flocks.

In the longitudinal surveys of 2 broiler flocks, A and B, gut content and kidney samples from about 12 birds, collected at timepoints from days 0 to 42, were tested for CAstV using the rRT-PCR test. Results obtained with the day 0 samples showed that CAstV RNA was detected in very few chickens and resulted in very low mean log values. At most timepoints after day 0, CAstV RNA was detected in all 12 or in the majority of samples tested, with the levels being higher in the gut contents than in the kidney (Table C). It was noted that were was not a substantial contrast between the CAstV RNA levels detected at early and late timepoints, particularly regarding levels detected with the gut content samples. For example, in flock A, CAstV RNA log values of 3.48 and 4.19 were observed for the gut content samples at days 28 and 35, while values of 3.76 and 2.61 were observed for the day 7 and day 14 samples. The CAstV RNA levels present in gut content and kidney samples at early timepoints was further investigated by testing day 4/5 and day 7 samples from 2 additional broiler flocks (Table D). With flocks C and D, samples were collected at day 4 and not at day 5 as was the case for flocks A and B. For the purposes of this study, the results obtained with the 4 flocks were compared at the day 4/5 timepoint and at the day 7 timepoint. With regards to the CAstV RNA levels in the gut content and kidney, no significant differences were observed between the 4 flocks at the day 4/5 and day 7 timepoints.

Detection of CAstV RNAs in Experimental Infection Samples.

One-day-old broiler chicks were infected orally with pooled gut content samples that were collected at days 4 and 7 from flock D. At 14 days p.i., the weights of the inoculated birds (n=20) were 21.4% less than those of the control, non-infected birds. Application of the CAstV real-time RT-PCR test to samples that were collected from groups of 5 experimentally infected chickens at different days post infection showed that CAstV RNA was detected in 20/30 (67%) gut content and 9/30 (30%) kidney samples that were collected up to day 28 p.i. (Table E). The levels of CAstV RNA were also considerably higher in the gut contents than in the kidneys, with the levels being significantly greater at early timepoints (days 7, 10 and 14) compared to later timepoints (days 21 and 28).

Although the invention has been particularly shown and described with reference to particular examples, it will be understood by those skilled in the art that various changes in the form and details may be made therein without departing from the scope of the present invention.

The invention claimed is:

1. A primer pair capable of amplifying a portion of a CAstV genome, wherein the primer pair comprises at least one oligonucleotide primer sequence that has binding specificity to a precapsid region of the CAstV genome;

wherein the precapsid region is defined as a 106 nucleotide region located at the 3' end of the polymerase gene, wherein the 106 nucleotide region comprises an intergenic region between the polymerase gene (orf1b) and the capsid gene (orf2) and the first four nucleotides of the capsid gene, and wherein the precapsid region has a polynucleotide sequence TGCGTCGAGGAGTATGCCGCTGCTGAAGAAATACAGTTACCAGAAGTCGGGC CCGACTTCTTTCAGAAAATCTGGTAGAGGGATGGACCGAAATATAGCA GCATGG (SEQ ID NO: 8); and wherein the primer pair comprises oligonucleotide primer sequences:

```
                                         (SEQ ID NO: 1)
forward primer GCYGCTGCTGAAGAWATACAG,
and (SEQ ID NO: 3)
reverse primer CATCCCTCTACCAGATTTTCTGAAA.
```

2. The primer pair of claim 1, wherein the primer pair consists of oligonucleotide primer sequences:

```
                                         (SEQ ID NO: 1)
forward primer GCYGCTGCTGAAGAWATACAG,
and (SEQ ID NO: 3)
reverse primer CATCCCTCTACCAGATTTTCTGAAA.
```

3. A method for detecting the presence of CAstV in a biological sample, the method comprising:

(a) performing a reverse transcription reaction, using as a template, RNA derived from the biological sample to produce CAstV specific reverse transcription products;
(b) amplifying the reverse transcription products by using a primer pair of claim 1 or claim 2; and
(c) performing a detecting step to detect the amplification product produced by the primer pair of claim 1 or claim 2;
wherein detection of the amplification product indicates the presence of CAstV RNA in the biological sample.

4. A method of amplifying and indicating the presence of CAstV cDNA, the method comprising:
(a) performing a polymerase chain reaction on a cDNA sample containing CAstV cDNA using a primer pair of claim 1 or claim 2; and
(b) performing a detecting step to detect the amplification product, wherein detection of the amplification product indicates the presence of CAstV cDNA in the sample.

5. The method of claim 3 or claim 4, further comprising providing at least one labelled oligonucleotide probe.

6. The method of claim 5, wherein the labelled oligonucleotide probe comprises 5'-FAM-CAGAAGTCGGGCCC-MGB (SEQ ID NO: 5).

7. A kit for use in the detection of CAstV, comprising a primer pair of claim 1 or claim 2.

* * * * *